Figure 1:
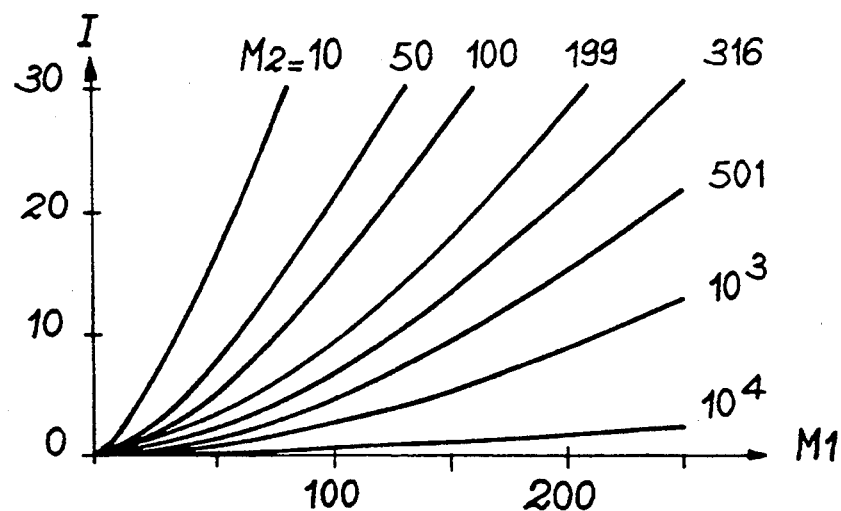

United States Patent [19]

Grenier et al.

[11] Patent Number: 5,373,538
[45] Date of Patent: Dec. 13, 1994

[54] SYSTEM FOR THE DETECTION OF SUBSTANCES AND IN PARTICULAR EXPLOSIVES BY THE NEUTRON IRRADIATION THEREOF

[75] Inventors: Gérard Grenier, Brevannes; Michel Rambaut, Bures-Sur-Yvette, both of France

[73] Assignee: Commissariat A L'Energie Atomique, Paris, France

[21] Appl. No.: 700,193
[22] PCT Filed: Oct. 2, 1990
[86] PCT No.: PCT/FR90/00701
  § 371 Date: Jun. 20, 1991
  § 102(e) Date: Jun. 20, 1991
[87] PCT Pub. No.: WO91/05272
  PCT Pub. Date: Apr. 18, 1991

[30] Foreign Application Priority Data

Oct. 3, 1989 [FR] France ............................ 89 12917

[51] Int. Cl.⁵ ............................................. G21G 1/06
[52] U.S. Cl. .................................... 376/159; 376/161; 376/166
[58] Field of Search ................. 376/159, 157, 161, 166

[56] References Cited

U.S. PATENT DOCUMENTS

| | | | |
|---|---|---|---|
| 2,938,119 | 5/1960 | McKay | 376/159 |
| 3,018,374 | 1/1962 | Pritchett | 376/159 |
| 3,124,679 | 3/1964 | Tittman et al. | 376/159 |
| 3,146,349 | 8/1964 | Jordan | 376/159 |
| 3,214,700 | 10/1965 | Hook . | |
| 3,315,077 | 4/1967 | Jones, Jr. et al. | 376/159 |
| 3,463,922 | 8/1969 | Senftle et al. | 376/159 |
| 3,492,479 | 1/1970 | Lowery et al. | 376/159 |
| 3,506,813 | 4/1970 | Trimble . | |
| 3,557,354 | 1/1971 | Trimble . | |
| 3,707,631 | 12/1972 | Untermyer | 376/159 |
| 3,736,429 | 5/1973 | Foley | 376/159 |
| 3,748,472 | 7/1973 | Smith | 376/159 |
| 3,781,556 | 12/1973 | Taylor et al. | 376/159 |
| 3,801,816 | 4/1974 | Arnold | 376/159 |
| 3,812,364 | 5/1974 | Higatsberger et al. | 376/159 |
| 3,832,545 | 8/1974 | Bartko | 376/159 |
| 3,832,545 | 8/1974 | Bartko | 376/159 |
| 3,942,003 | 3/1976 | Apenberg et al. | 376/159 |
| 3,997,787 | 12/1976 | Fearon | 250/359 |
| 4,008,392 | 2/1977 | Lock et al. . | |
| 4,024,393 | 5/1977 | Braun et al. | 376/159 |
| 4,028,267 | 6/1977 | Ragnar et al. | 376/159 |
| 4,171,485 | 10/1979 | Marshall | 250/359 |

(List continued on next page.)

FOREIGN PATENT DOCUMENTS

| | | |
|---|---|---|
| 0227497 | 7/1987 | European Pat. Off. . |
| 2201765 | 4/1974 | France . |
| 424039 | 9/1974 | U.S.S.R. . |

OTHER PUBLICATIONS

Glenn Knoll, Radiation Detection and Measurement, Joan Wiley & Sons.

(List continued on next page.)

*Primary Examiner*—Donald P. Walsh
*Assistant Examiner*—Frederick H. Voss
*Attorney, Agent, or Firm*—Oblon, Spivak, McClelland, Maier & Neustadt

[57] ABSTRACT

System for the detection of substances and in particular explosives, by neutron irradiation thereof.

It comprises means (4) for the irradiating, by neutrons, of an object (6) which may contain a substance, means (14) for detecting the gamma radiation which can be emitted by the object and means (18) for processing the signals supplied by the detection means. These processing means count the gamma photons of each line of a plurality of characteristic lines of at least one chemical element of the substance, determining for each line a probability of false detection of the chemical element associated with said line, determine the product of these probabilities, compare said product with a threshold fixed by users and notify the latter if the product is below the threshold, the object then being assumed to contain the substance.

20 Claims, 5 Drawing Sheets

U.S. PATENT DOCUMENTS

| | | |
|---|---|---|
| 4,209,695 | 6/1980 | Arnold et al. |
| 4,251,726 | 2/1981 | Alvarez ............... 376/157 |
| 4,263,098 | 4/1981 | Kasperek et al. |
| 4,266,132 | 5/1981 | Marshall ............... 376/159 |
| 4,268,754 | 5/1981 | Srapeniants et al. ............... 376/159 |
| 4,272,891 | 6/1981 | Fusari . |
| 4,278,885 | 7/1981 | Alfthan et al. ............... 376/159 |
| 4,291,227 | 9/1981 | Caldwell et al. ............... 376/159 |
| 4,314,155 | 2/1982 | Sowerby ............... 376/159 |
| 4,358,738 | 11/1982 | Kahn . |
| 4,367,490 | 1/1983 | Riederer . |
| 4,408,284 | 10/1983 | Kijesky et al. . |
| 4,517,680 | 5/1985 | Betts et al. . |
| 4,665,486 | 5/1987 | Schultz . |
| 4,682,045 | 7/1987 | Amazawa et al. . |
| 4,724,118 | 2/1988 | Grenier ............... 376/159 |
| 4,782,456 | 11/1988 | Poussier et al. . |
| 4,837,720 | 6/1989 | Rambaut . |
| 4,851,687 | 7/1989 | Ettinger et al. ............... 376/159 |
| 4,882,121 | 11/1989 | Grenier ............... 376/159 |
| 5,098,640 | 3/1992 | Gozani et al. ............... 376/159 |

OTHER PUBLICATIONS

Nucleonics, Sep. 1965, pp. 70–78, Tilbury et al.
Pure & Appl. Chem., vol. 49, pp. 1555–1573, (1977) Gijbols et al.
*Modern Methods for Trace Element Analysis,* Ann Arbor Sci. Pub. Inc. 1978, Chap. 9, pp. 370, 371, 390, 391, 398–403, Pinta.
Radiochem. Radioanal. Letters, vol. 12, No. 4–5, (1972), pp. 283–288, Anisimov et al.
J. of Radioanalytical and NuclearChemistry, Articles, vol. 84, (1984), pp. 67–87, Nadkarni.
Journal Nucleonics, Aug. 1966, vol. 24, No. 8, pp. 118–121.
Nuclear Instruments and Methods, Mar. 1983, vol. 206, No. 3, pp. 501–506.
Health Physics, Jan. 1977, vol. 32, No. 1, pp. 1–14.
Nucleonics, vol. 24, No. 8, Aug. 1966, pp. 118–121, New York, U.S.; W. L. Nicholson: "Statistics of Net–Counting-Rate . . . Background Corrections".
Health Physics, vol. 32, No. 1, Jan. 1977, pp. 1–14, Pergamon Press, Oxford, GB J. J. Donn et al.: "The Statistical Interpretation of Counting Data from Measurements of Low-Level Radioactivity".
Nuclear Instruments & Methods, vol. 206, No. 3, Mar. 1983, pp. 506–506, North-Holland Publishing Co., Amsterdam, NL; T. J. Sumerling: "Calculating a Decision Level for Use in Radioactivity Counting Experiments".

SYSTEM FOR THE DETECTION OF SUBSTANCES AND IN PARTICULAR EXPLOSIVES BY THE NEUTRON IRRADIATION THEREOF

DESCRIPTION

The present invention relates to a system for the detection of substances and in particular explosives by the neutron irradiation thereof. It more particularly applies to the checking of luggage, especially in airports.

Systems for the detection of explosives involving the irradiation of the latter by neutrons are already known and reference can be made to FR-A-2201765 and EP-A-0227497.

It is pointed out that there are three processes for producing gamma photons by the interaction of neutrons with nuclei:

the capture of a neutron by a nucleus producing an isotope, which is deexcited by the emission of a gamma radiation and which is referred to by capture gamma radiation, said interaction essentially taking place with thermal neutrons;

the inelastic scattering of a neutron on a nucleus, which is deexcited by the emission of prompt gamma radiation, said interaction only existing with fast neutrons having an adequate energy (i.e. an energy at least equal to that of the prompt gamma radiation); and the activation of a nucleus by a thermal or fast neutron, which creates a radioactive nucleus having a certain life and which disintegrates on emitting activation gamma radiation.

In addition, standard explosives have carbon, hydrogen, oxygen and nitrogen atoms and the most interesting elements for the detection of the presence of an explosive are nitrogen and oxygen, particularly due to the separability of the gamma lines or peaks, created by the inelastic scattering of fast neutrons, the energy of the gamma photons being between 2.3129 and 6.1304 MeV.

The use of capture gamma radiation for nitrogen at 10.83 MeV is also of interest due to the good signal-to-noise (S/N) ratio in the energy range close to 10 MeV.

The aforementioned, known detection systems suffer from the disadvantage of giving rise to an excessive probability of a lack of detection (approximately $10^{-2}$ or more) in the case of checks carried out at high speeds and for small explosive quantities.

The present invention aims at obviating this disadvantage by proposing a system for the detection of substances and in particular explosives, which makes it possible to reduce this lack of detection probability and to even reach very low values for the same ($10^{-4}$, $10^{-10}$ or even less than $10^{-10}$) using high resolution detection means for detecting the gamma radiation.

More specifically, the present invention relates to a system for the detection of a substance which may be contained in an object, characterized in that it comprises:

means for irradiating the object by thermal and/or fast neutrons, means for detecting the gamma radiation which may then be emitted by the object and electronic means for processing the signals supplied by the detection means, said electronic processing means being provided for counting the gamma photons corresponding to each line of a plurality of characteristic lines of at least one chemical element of the substance, determining, for each line i, a false detection probability for the chemical element associated with said line, i.e. the probability PFi of the detected signal corresponding to said line i being due to a background noise, determining the product of these false detection probabilities, comparing this product with a threshold fixed by the system users and notifying these users if the product is below the threshold fixed by them, the object then being assumed to contain the substance.

Therefore the important elements of the invention making it possible to reduce the lack of detection probability compared with known systems are:

the choice of one or a plurality of chemical elements contained in the substance which it is wished to detect, e.g. nitrogen alone or nitrogen and oxygen or nitrogen, oxygen and carbon in the case of an explosive, the choice of a plurality of lines characteristic of the element or elements chosen and whereof the corresponding gamma photons are counted, e.g. in the case of an explosive, the lines at 5.106 MeV and at 10.83 MeV of nitrogen or one and/or the other of the preceding lines, together with one or more characteristic lines of oxygen and optionally, in addition, respectively characteristic lines of elements such as carbon, hydrogen and chlorine (chloro explosive) and evaluating the false detection probability relative to each of these lines (or an information quantity linked with this probability).

Each false detection probability PFi can be determined by the formula:

$$PFi = e^{-M'2i} \sum_{j=Ni+1}^{+\infty} \frac{M'2^j}{j!}$$

in which Ni represents the count, during a time Dt, which corresponds to the line i and which is due to nuclear reactions induced by neutrons and also to a background noise M'2i relative to the line i during the time Dt.

Each background noise M'2i can be determined by forming the sum of a physical background noise M2i, relative to the line i, and the upper limit Ci of the counts relative to the said line i, during the time Dt, on objects liable to contain the substance, but which are known not to contain it.

According to a first embodiment of the system according to the invention, the electronic processing means are provided for:

determining, for each line i, an information quantity Ii relative to the said line i and defined by the formula:

$$Ii = -\log \frac{PFi}{1 - PFi}$$

(after determining Ni and then PFi), determining the sum of these information quantities, comparing said sum with a threshold fixed by the system users and notifying said users if said sum exceeds the threshold with which it is compared, the object then being assumed to contain the substance.

According to a second embodiment, allowing a shorter calculation time and therefore a shorter object checking time, the electronic processing means are provided for:

determining, for each line i, an information quantity Ii relative to the said line i and defined by the formula:

$$Ii = K(M'2i) \cdot \frac{N1i^{a(M'2i)}}{M'2i^{\frac{1}{2}}}$$

(after determining Ni, but without having to determine PFi), in which K and a are stored functions of a background noise M'2i relative to the line i and N1i is the integral part of the difference Ni−M'2i, Ni representing the count, during a time Dt, which corresponds to the line i and which is due to nuclear reactions induced by neutrons and also to the background noise M'2i relative to the line i, during the time Dt, determining the sum of these information quantities, comparing said sum with a threshold fixed by the system users and notifying these users if said sum exceeds the threshold with which it is compared, the object then being assumed to contain the substance.

The system according to the invention is applicable both to a "closed" configuration and to an "open" configuration.

The irradiation means can comprise a fast neutron source and an enclosure for thermalizing said fast neutrons, in which is located the source and which serves to receive the object, or can comprise a fast neutron source for irradiating the object, i.e. directly and without a thermalization enclosure.

In order to be able to check the entire object, the detection means can comprise a plurality of gamma radiation detectors, the electronic processing means having a plurality of detection chains, respectively associated with the detectors and the configuration of the detectors can be of a matrix type.

According to a preferred embodiment of the system according to the invention, which makes it possible to greatly reduce the lack of detection probability compared with known systems, the gamma radiation detection means are high resolution detection means. To this end, it is e.g. possible to use one or a plurality of high purity germanium detectors.

Preferably, the irradiation means incorporate a neutron source, the detection means being protected from direct radiation from the source and are collimated towards the object.

In a preferred embodiment of the invention, the irradiation means incorporate a pulsed neutron source for supplying neutron bursts and the electronic processing means cooperate with the detection means for carrying out measurements in the time intervals where it is certain that there is only a detection of one of the categories of gamma photons produced during the irradiation of the object by neutrons.

This pulsed neutron source is e.g. used for a synchronous detection of prompt gamma photons and a detection of capture gamma photons between neutron bursts. Thus, for each type of detection, it is possible to obtain a S/N ratio well above that obtained with a continuous neutron source.

In the present invention, the irradiation means preferably have a 14 MeV neutron source produced by fusion reactions. Thus, a neutron source with such an energy makes it possible to check most chemical elements.

Finally, in a special embodiment of the invention appropriate for the detection of explosives, the electronic processing means count the gamma photons of a plurality of lines, which respectively characterize nitrogen, oxygen and possibly carbon, in the case of nitro explosives, or other elements in the case of other explosives.

The invention is described in greater detail hereinafter relative to non-limitative embodiments and with reference to the attached drawings, wherein show:

FIG. 1 a graph illustrating the variation of the information quantity as a function of the average signal level, for a constant physical noise level and for various physical noise levels.

Figure 2:
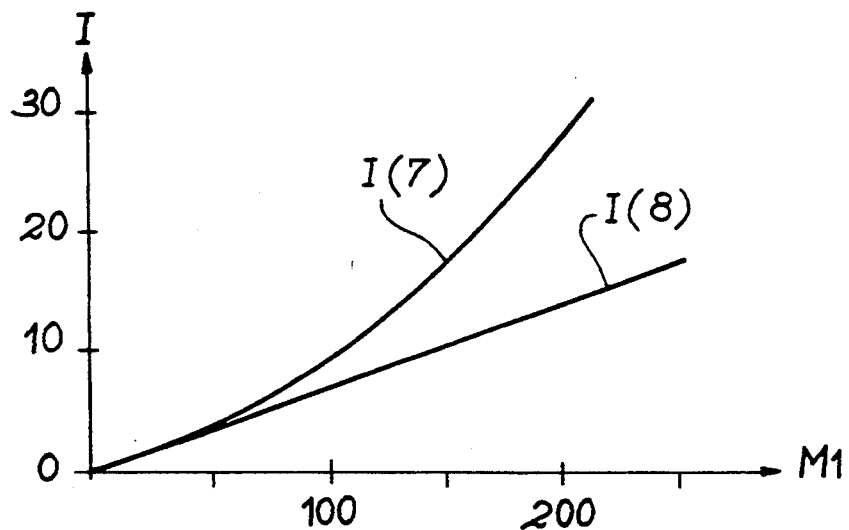

FIG. 2 a graph making it possible to compare the two expressions of the information quantity.

Figure 3:
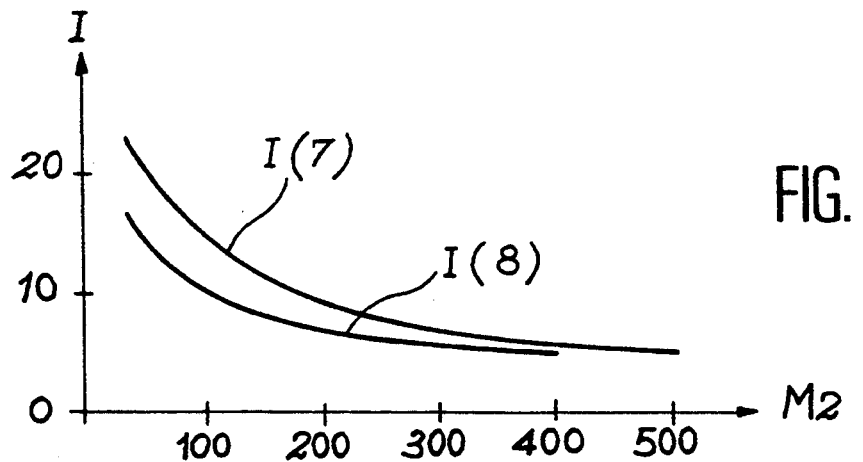

FIG. 3 a graph showing the monotonic decrease, as a function of the physical noise level, of each of the two expressions of the information quantity.

Figure 4:
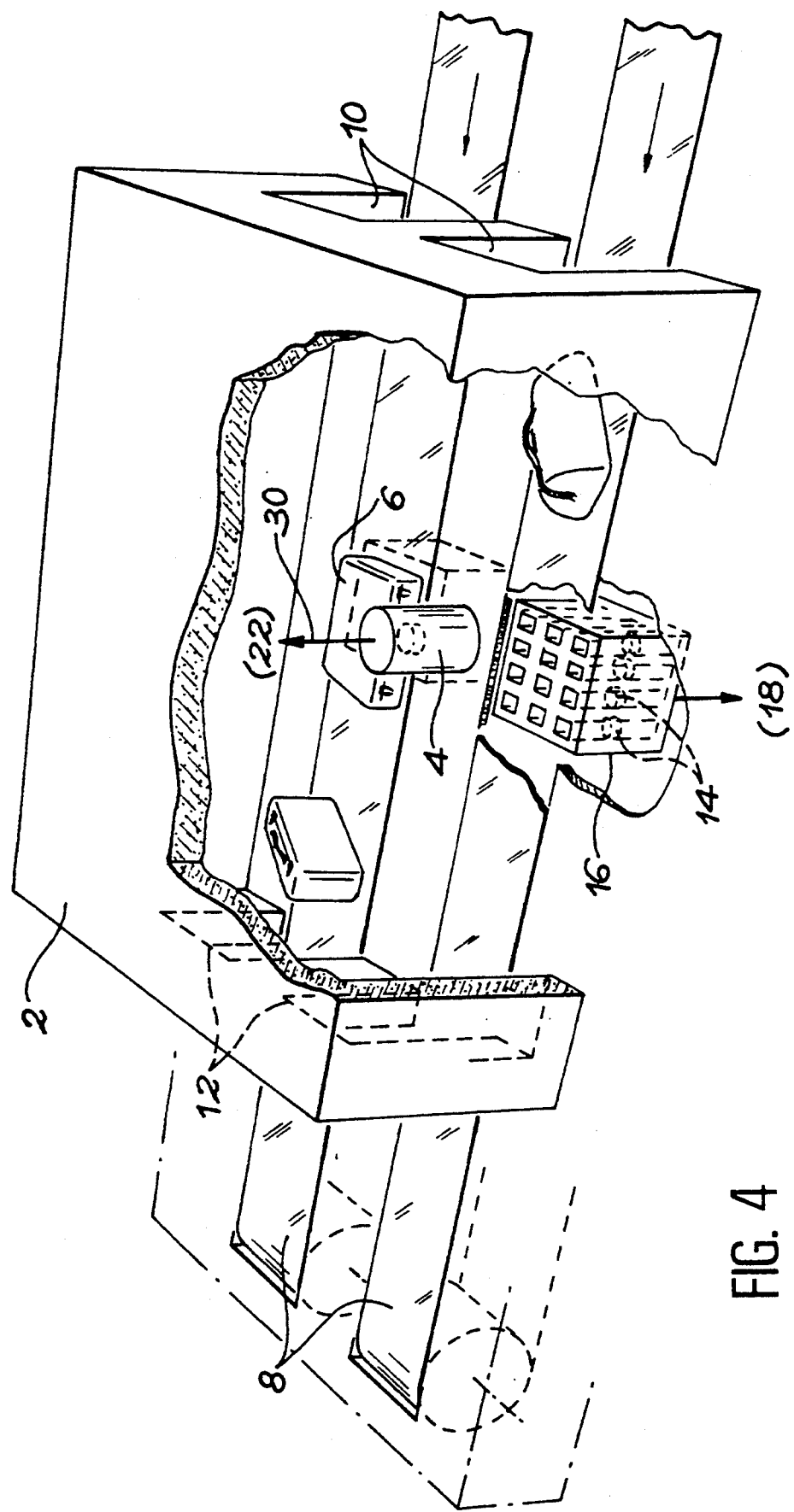

FIG. 4 a diagrammatic perspective view of an embodiment of the system according to the invention using a plurality of fixed gamma radiation detectors and a thermalization enclosure.

Figure 5:
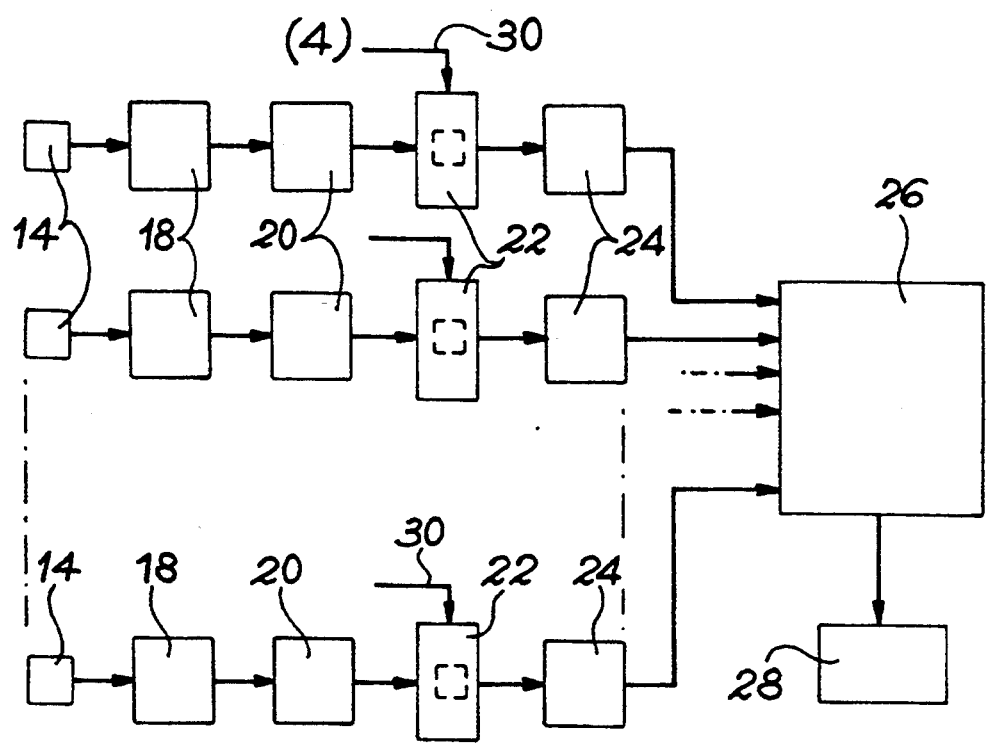

FIG. 5 diagrammatically electronic processing means usable for processing the pulses supplied by these detectors.

Figure 6:
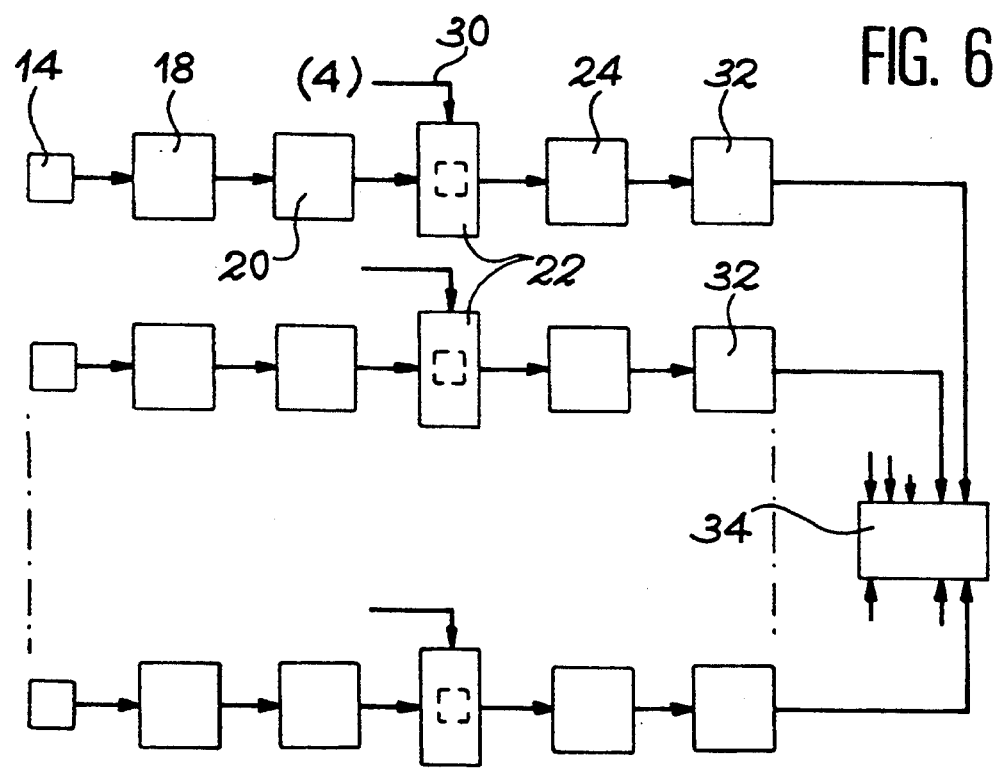

FIG. 6 diagrammatically other electronic processing means also usable for processing pulses supplied by the detectors shown in FIG. 4.

Figure 7:
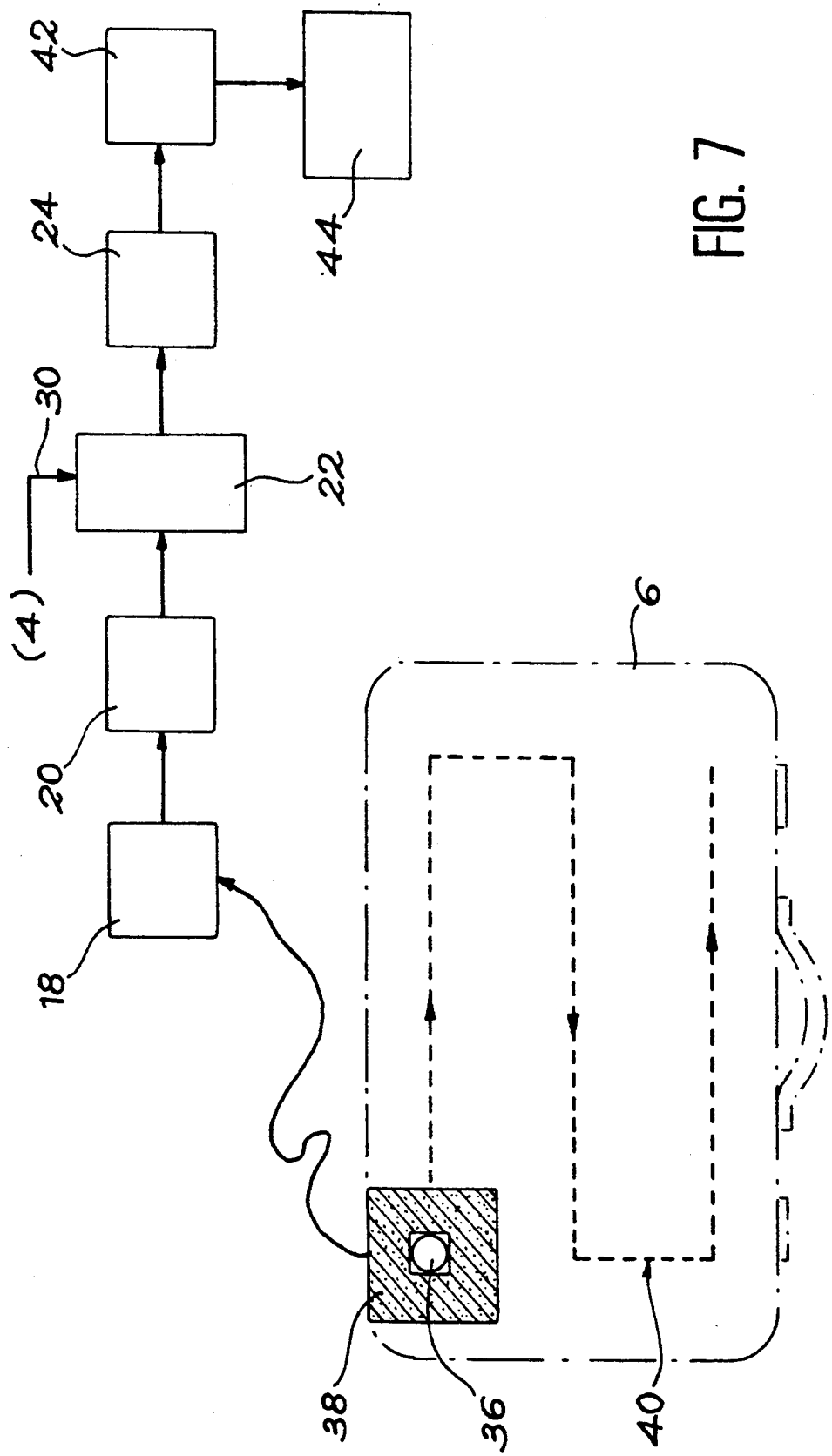

FIG. 7 a diagrammatic, partial view of another embodiment of the system according to the invention using a mobile gamma radiation detector.

Figure 8:
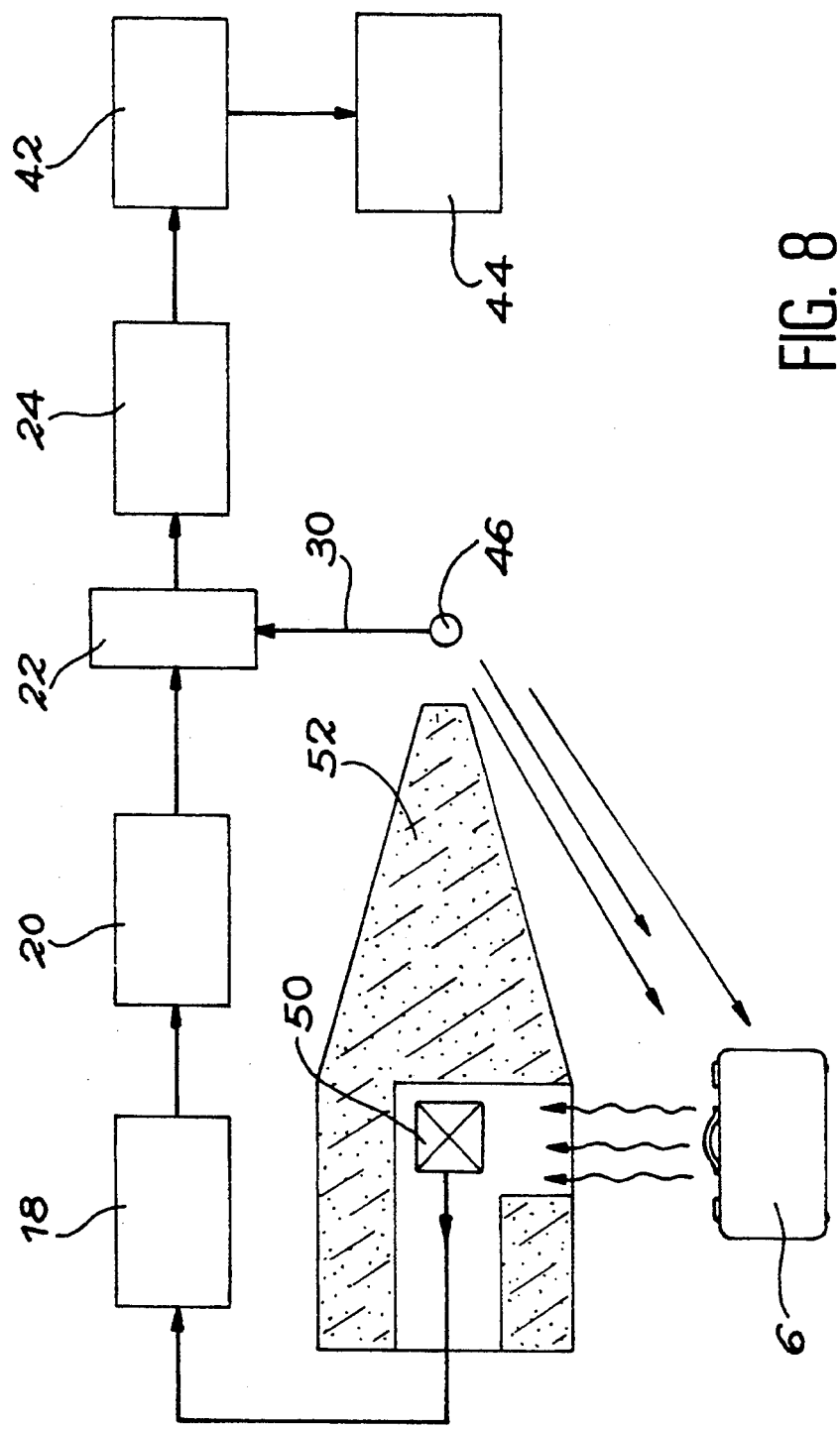

FIG. 8 a diagrammatic view of another embodiment of the system according to the invention with an "open" configuration.

Hereinafter, it is assumed that it is wished to check luggage liable to contain explosives and e.g. nitro explosives.

Only a limited time is available for each piece of luggage in order that an adequate flow rate is ensured, which is measured in the number of items per hour. This period of time is e.g. a few seconds.

An item of luggage is brought up to a system according to the invention, where it is irradiated by neutrons and a count is carried out for a time Dt of the gamma photons and these obviously include the gamma photons emitted by the object as a result of its irradiation.

With said time Dt corresponds an average number of events M2 due to various physical causes (movement of the gamma radiation detector or detectors, radiation of the surrounding medium, cosmic radiation, etc.) and which is referred to as "physical background noise". For the said same time Dt, there is an average count M1 which can be attributed to the presence of a suspect product, e.g. a nitrogenous material.

Tests carried out on a large number of luggage items demonstrate that a typical item of an "average" traveller corresponds to a maximum count Ci under a peak i, said maximum count being attributable e.g. to nitrogenous material (the peak i being e.g. the peak at 10.83 MeV of nitrogen) without the luggage containing any explosive quantity.

Any count exceeding the sum M2i+Ci, in which M2i is the value of the count due to the physical background noise beneath the peak i during the time Dt, will be attributed to the presence of an explosive. For the detection of an abnormal nitrogen quantity which can be attributed to an explosive, it is considered that there is a background noise $M'2i$ such that $$M'2i = M2i + Ci \qquad (1)$$

In accordance with the present invention, it is decided beforehand to examine a certain number of lines i, i ranging between 1 and n, in the gamma radiation spectrum and the presence of each line i is characterized by the probability PFi that the detected signal is due to background noise or to a suspect material quantity below the upper limit of the normal quantity in other words there is a false detection.

With the "rough" count Ni beneath the peak i and the average noise count $M'2i$ is made to correspond a false detection probability PFi such that:

$$PFi = e^{-M'2i} \sum_{j=Ni+1}^{+\infty} \frac{M'2^j}{j!} \qquad (2)$$

Moreover, the value N1i is considered equal to the integral part of the difference between the rough count Ni beneath the peak i and $M'2i$, i.e.:

$$N1i = E(Ni - M'2i) \qquad (3)$$

designating by $E(x)$ the integral part of the number x.

With the value N1i and the value $M'2i$ of the background noise is made to correspond a lack of detection probability PDi characterizing the inevitable deficiency or shortcoming of the system of not detecting what it should detect, said detection deficiency probability being such that:

$$PDi = e^{-(N1i+M'2i)} \sum_{k=0}^{E(M'2i)} \frac{(N1i + M'2i)^k}{k!} \qquad (4)$$

It can be demonstrated that with a rising background noise $M'2i$, that PDi and PFi tend towards the same value, PDi remaining higher than PFi, the probability PDi constituting a fundamental evaluation element for knowing the aptitude of the system of not missing an item of luggage containing an explosive charge.

However, in the present invention, use is made of the probability PFi in view of its "operational" importance (and the fact that PDi and PFi tend towards the same value).

In the present invention, it is also possible to measure the information obtained during the time Dt by means of a function called the "information quantity" and designated Ii for the line i, said quantity Ii being dependent on the probability of false detection PFi obtained during gamma photon storage.

Each information quantity satisfies the following conditions:

additivity of the information quantities obtained during two separate storages, carried out under the same conditions and nullity of the information quantity before any storage.

The false detection probabilities PF' and PF" on a particular phenomenon, during two separate counts, are independent, so that the false detection probability PF resulting from the two counts considered together has as its expression:

$$PF = PF' \times PF'' \qquad (5)$$

The following expression is then chosen for the information quantity Ii:

$$Ii = -\log \frac{PFi}{1 - PFi} \qquad (6)$$

Prior to the measurement, the true and false detection probabilities are a priori equal to 0.5 and the expression (6) of the information quantity is then zero. It is also zero in the case where the count Ni is equal to the average background noise count M2i, because PFi is then equal to 0.5. The information quantity Ii is positive if the count Ni exceeds M2i and negative if Ni is below M2i.

It should be noted that it would be possible to change the sign of the information quantity by changing the criterion (obtaining an information quantity Ii' on the non-existence of a particular phenomenon with Ii' = -Ii).

Reference should be made to the following documents in connection with this information quantity notion:

Article by M. L. Rambaut, entitled "Detection d'un rayonnement corpusculaire et information" and published in Nuclear Instruments and Methods in Physics Research A248 (1986), pp. 471–482, North Holland, Amsterdam;

EP-A-0200596,

EP-A-0202980,

French patent application 8712970 of Sep. 18 1987.

In FIG. 1 has been plotted the curve of the information quantity variations I as a function of the average or mean signal level M1, expressed as a number of events during the time Dt and for a constant noise M2 expressed as the number of events during the time Dt for several values of M2 (10, 50, 100, 199, 316, 501, $10^3$ and $10^4$) the base of the logarithm being equal to 10 and the information quantity being expressed in digits.

The group of curves in FIG. 1 quantitatively shows the advantage of placing the gamma radiation detector or detectors at the point where the noise M2 is at a minimum.

The system according to the invention can comprise a fission neutron source, e.g. a californium 252 source.

However, the said system advantageously comprises a pulsed neutron source of fusion 14 MeV. Thus, if the measurement is only carried out in the time interval where there is a certainty of detecting one of the three aforementioned gamma photon categories, it is possible to proportionally reduce the storage time and therefore the value of the background noise.

Instead of using the formula (6) for the information quantity ii, it is possible to use a semi-phenomenological formula which can be deduced from the formulas (2) and (6) and which is as follows:

$$Ii = K(M'2i) \cdot \frac{N1i^{a(M'2i)}}{M'2i^a} \qquad (7)$$

in which K and a are functions of $M'2i$.

This formula (7) is based, via formula (2), on the calculation of probabilities and facilitates the dialogue between the system according to the invention and its users. It is also preferable to a formula of type:

$$Ii = \frac{N1i}{M'2i^{\frac{1}{2}}} \qquad (8)$$

Thus, on considering FIG. 2, in which an information quantity I(7) according to formula (7) and an information quantity I(8) according to formula (8), expressed in digits, are represented as a function of a signal level M1, for a fixed noise M2 equal to 199 (events due to the physical noise during the time Dt), it can be seen that the expression of the formula (7) supplies more information than that of formula (8).

The choice of the gamma radiation detection means is important for the present invention. It is possible to choose one or more low resolution detectors, e.g. using sodium iodide crystals, or very high resolution detectors e.g. using bismuth germanate crystals and having a relatively low cost. However, such detectors do not provide an adequate guarantee to users of the system, in view of the fact that their use leads to an excessively high probability PD of not detecting an explosive.

Thus, according to the present invention, preference is given to the use of one or more high resolution detectors, e.g. having an intrinsic germanium crystal. Such detectors make it possible to separate all the useful gamma photon peaks (whereof some would not even be visible on a spectrum obtained with a low resolution detector) and to have beneath a gamma peak a maximum S/N ratio, so that the maximum information quantity would be obtained in a given time Dt.

As will be shown hereinafter, the use of such high resolution detectors in combination with the use of false detection probabilities (or information quantities of the type of formulas (6) or (7)) makes it possible to considerably lower the probability of a lack of detection of an explosive to levels well below $10^{-2}$.

It would certainly be possible to use low resolution detectors whilst increasing the neutron flux per unit of time. However, this would lead to an increase in the magnitude of radiation protection problems inherent in explosive detection systems by neutron irradiation and would in particular lead to pile-ups in analog electronic circuits for processing signals supplied by gamma radiation detectors.

To reduce PF and PD and to increase the information quantity, there is consequently an increase of the resolution of the detection means, which leads to a reduction of noise in the same proportion.

If it is assumed that the probability density beneath a peak i, as a function of the energy of the gamma photons, is gaussian, then the standard deviation s of the count of the events is proportional to the physical background noise M2i beneath the peak. Thus, by eliminating the index i for greater simplicity and considering two detectors referenced only by the indices A and B, it is possible to write:

$$sA/sB = M2A/M2B \qquad (9)$$

Consequently, as the efficiency levels of the detectors and the counts due to the signal are assumed to be identical and therefore also identical in both detectors, if the information quantities IA and IB, respectively corresponding to the detectors A and B, are expressed by the formula (8), it is found that each of these information quantities IA and IB obtained during the same time Dt is inversely proportional to the square root of the corresponding standard deviation.

Conversely, if the formula (7) is used for calculating the information quantities IA and IB, if the signal level M1A is equal to the signal level M1B and if the noise M2A is below the noise M2B, the ratio IA/IB is below the ratio $sB^{\frac{1}{2}}/sA^{\frac{1}{2}}$. This is due to the fact that the information quantity expressed by the formula (7) decreases in monotonic manner as a function of the noise, whilst remaining above the information quantity expressed by the formula (8), as can be seen in FIG. 3, where a choice has been made of a particular value of the count in the signal channel, namely M1=100 events during the time Dt.

For example, consideration will be given to the case of the line at 10.83 MeV of nitrogen and a standard deviation of approximately 500 keV is used for the index B detector, which typically characterizes the low resolution of a bismuth germanate detector. It is considered that the width of the energy band around 10.83 MeV, in which the gamma photons are detected, is equal to 1.3 MeV. For the index A detector, a standard deviation of 10 keV is used and an energy band of width 20 keV around 10.83 MeV, which typically corresponds to an intrinsic germanium detector. A ratio IA/IB greater than 8 is then obtained. More specifically, on applying formula (2), to values of approximately $10^{-2}$ for PF and PD (M2=120 and M1=130 events during the time Dt), said values being accessible with the aid of a low resolution detector, for a high resolution detector a value close to $10^{-26}$ is obtained and consequently there is a virtually absolute detection security or reliability.

It should also be noted that high resolution detection means make it possible to increase the baggage flow rate per unit of time by reducing the "storage" time, with a view to obtaining an intermediate value between $10^{-2}$ and $10^{-26}$ for PF and PD.

FIG. 4 is a diagrammatic, partial perspective view of a system according to the invention used for checking baggage in order to ensure that it contains no explosives.

The system shown in FIG. 4 comprises a neutron thermalization enclosure 2 and, in the latter, e.g. in its centre, a fast neutron source 4, e.g. a 14 MeV neutron source. The enclosure 2 is made from a material able to thermalize the fast neutrons, e.g. a hydrogencontaining material such as polystyrene.

In order to gain time, the system makes it possible to check two items of luggage 6 at the same time and for this purpose has two conveyor belts 8 traversing the enclosure 2 and making it possible for the luggage items 6 to travel on either side of the source 4. For each conveyor belt 8, the enclosure has an inlet 10 enabling the luggage items to enter the enclosure and an outlet 12 enabling them to leave it.

The conveyor belts 8 are made from a thin material having a low absorption with respect to gamma radiation and containing the minimum quantity of the elements which it is wished to detect.

The system shown in FIG. 4 also comprises means for detecting the gamma radiation emitted by baggage when irradiated by neutrons. These detection means incorporate, for each conveyor belt 8, an array of preferably high resolution detectors 14.

Each array of detectors 14 is positioned beneath the corresponding conveyor belt 8, level with the source 4, in such a way that each luggage item 6 to be checked and which travels on the conveyor belt, preferably resting thereon by its largest surface, can be brought into the presence of the source 4 and the array of detectors corresponding to said conveyor belt.

In a not shown variant, the arrays of detectors are placed on either side of the source between the two belts and not beneath their respective belts.

FIG. 4 shows that each detector 14 is protected against direct radiation from the neutron source and is collimated towards the luggage item 6 to be checked. Use is made for this purpose of a block or shield 16 made from a material able to stop neutrons and in which are provided recesses for receiving in each case one detector 14.

FIG. 5 diagrammatically illustrates electronic means for processing pulses supplied by the detectors 14 (which function simultaneously). These electronic processing means incorporate a plurality of detection chains. Each detector 14 is associated with a detection chain, which successively comprises, following the associated detector 14, a preamplifier 18, a proportional amplifier 20, a gate-equipped discriminator 22 and an amplitude coder 24.

The integral linearity and differential linearity of the amplitude coder must be adequate to fully exploit the possibilities offered by the use of a high resolution detector.

The number and arrangement of the detectors are dependent on the shape and dimensions of the luggage to be checked. The number of detectors and therefore the detection chains is also dependent on the solid angle observable by a detector, the maximum value of PF chosen for characterizing the presence of an explosive and the number of neutrons emitted by the source per unit of time.

As can be seen in FIG. 5, the amplitude coders are connected to a computer 26, which is itself connected to signalling means 28 (able to display the results of a check and/or emit a sound signal if a checked item of luggage is assumed to contain explosives), the computer receiving the values of the amplitude codings relating to each chain.

Preferably, the source 4 is a pulsed source able to supply neutron bursts and, as shown in FIGS. 4 and 5, said pulsed source is connected to each of the gate-equipped discriminators 22 by a synchronizing line 30, with a view to carrying out the detection of prompt gamma photons coinciding with the fast neutron bursts and the detection of capture gamma photons between said neutron bursts.

The system shown in FIGS. 4 and 5 functions as follows. An item of luggage placed on a conveyor belt 6 enters the thermalization enclosure 2 and is brought into the presence of the source 4 and the array of detectors 14 corresponding to the said belt. The source emits fast neutrons, which are thermalized by the enclosure walls, so that the luggage is also irradiated by the thermal neutrons and essentially emits prompt, capture and activation gamma photons. The detectors 14 of the array receive these gamma photons and supply signals to the electronic processing means, which process them in the following way.

It is assumed that it has been decided to examine lines of nitrogen and lines of oxygen in an exemplified manner. The computer has in its memory the quantity M'2i corresponding to the line i for each of the n chosen lines. Each detection chain enables the computer 26 to acquire a count value Ni for each line i. Therefore the computer is able to calculate, by means of the formula (2), the probability PFi for each line i and for each detection chain. Then, for each detection chain, the computer 26 calculates the quantity PF equal to the product of the quantities PFi in accordance with the following formula:

$$PF = \prod_{i=1}^{n} PFi \qquad (10)$$

PF being the probability that all the counts performed under all the peaks considered to be relevant for the detection of explosives are due solely to noise or to an explosive quantity below the maximum quantity present in luggage containing no explosive.

Then, for each detection chain, the computer 26 compares PF with a threshold S1 fixed by the users. If, for at least one of the detection chains, PF is below S1, the luggage is assumed to contain an explosive and the computer then controls the signalling means 28. This suspect luggage item is then directed to a suspect luggage storage zone for examination there.

If, however, PF is at least equal to S1 for each of the detection chains, the luggage item is considered to contain no explosive and leaves the thermalization enclosure 2 by the outlet corresponding to the conveyor belt on which the luggage is located.

In a constructional variant of the system shown in FIGS. 4 and 5, the computer calculates, for each detection chain, the probability PFi for each line i and then, by formula (6), the corresponding information quantity Ii. Then, the computer calculates the sum of these information quantities for each detection chain. Each sum is then compared with a threshold S2 fixed by the users.

If the sum exceeds S2 for any random one of the detection chains, the luggage item is assumed to contain an explosive, the users are notified thereof and the luggage is directed to the suspect luggage zone. If, however, the sum is equal to or below S2 for each of the detection chains, the luggage is considered to contain no explosive and leaves the thermalization enclosure.

In another variant, instead of using formula (6) for calculating the information quantity Ii, use is made of formula (7), the computer having in its memory the functions K and a, which leads to a shorter calculation time.

FIG. 6 illustrates in diagrammatic manner other electronic means for processing the pulses supplied by the detectors 14. These other electronic processing means differ from those of FIG. 5 as a result of the fact that the computer 26 is replaced by a plurality of processors 32, which are respectively associated with the detection chains (each having the elements 18, 20, 22 and 24), each processor 32 being positioned following the corresponding coder 24 and connected to the latter.

In the case of the electronic processing means shown in FIG. 6, each processor 32 calculates the product PF (or the sum of the information quantities) for the detection chain with which it is associated. All the processors 32 are connected to signalling means 34 making it possible to notify the system users when, as a result of at least one of the detection chains, it is assumed that an explosive is present.

FIG. 7 diagrammatically and partially shows another detection system according to the invention, which differs from that of FIG. 4 by the fact that it uses a single high resolution detector 36 in place of an array of such detectors, said detector 36 being positioned as previously and located in means 38 for collimating and providing protection with respect to the direct radiation of the source 4.

Not shown means permit the displacement of the detector 36, associated with the means 38, in accordance with a path 40 enabling it to check the entire luggage 6, which is immobilized.

The signals supplied by the detector 36 are fed to a detection chain which, as hereinbefore, comprises a preamplifier 18, a proportional amplifier 20, a gate-equipped discriminator 22 and an amplitude coder 24, the latter being connected to a computer 42, which is connected to signalling means 44.

The displacement means of the detector 36 make it possible to stop the latter beneath the luggage item 6 at different points and, if no explosive has been detected at each of these points, the luggage is considered to contain no explosive, whereas if at one of these points the presence of explosive is presumed, the luggage is directed towards the suspect luggage zone for examination there.

FIG. 8 diagrammatically and partially shows another detection system according to the invention. This system differs from that shown in FIG. 4 by the fact that it has an "open" configuration and consequently has no neutron thermalization enclosure. The system of FIG. 8 also has a pulsed fast neutron source 46 brought into the presence of the luggage to be checked.

The system shown in FIG. 8 also comprises a high resolution detector 50 for detecting gamma radiation and, as previously, said detector is connected to a detection chain of the type shown in FIG. 7, said chain being connected to a computer, which is itself connected to signalling means.

As previously, the source 46 is connected by a synchronizing line to the gate-equipped discriminator of the chain for reasons explained hereinbefore. In addition, the detector 50 is protected from the direct radiation from the source 46 and collimated, by appropriate means 52 towards the baggage 6 to be checked.

Thus, each baggage to be checked is positioned facing the collimated detector 50, the source 46 being positioned in such a way as to be able to irradiate the baggage 6 with the fast neutrons which it generates, so that the baggage 6 essentially emits gamma radiation due to the fast neutrons and which reaches the detector 50. The pulses emitted by the latter are processed by the electronic processing means associated with the said detector 50.

It would obviously be possible to use in place of a single detector an array of detectors, each detector of said array being associated with a detection chain, in the manner explained relative to FIGS. 5 and 6.

The present invention is not limited to the detection of nitro explosives. It can also be used e.g. for the detection of non-nitro explosives and even for the detection of a large number of chemical compounds, whilst making use of the gamma signatures relative to the chemical elements of said compounds.

The invention more particularly applies to the detection of narcotics, making particular use of the nitrogen and carbon peaks.

Using as an example the check carried out on luggage to ensure that it does not contain explosives, an explanation will now be given of the prior obtaining of parameters and functions ($M2i$, $Ci$ $1 \leq i \leq n$, $K$ and $a$) which should be stored for carrying out the various calculations. The phsyical background noise $M2i$ beneath the peak i is estimated by extrapolating the probability density on either side of said peak.

The maximum contribution ($Ci$) to the count of the non-explosive materials of a typical luggage item is measurable if a sufficient number of luggage items is available and which are filled with normal products (clothing, toilet articles, etc.). Such explosion-free luggage is passed into the system of FIG. 4, being successively placed in front of the system of FIG. 8 and then various counts are made and the mean is formed therefrom in order to obtain $Ci$.

It should be noted that the calculation of PFi can be carried out directly on the basis of formula (2), or by tabulating the values of PFi as a function of Ni and M2i, e.g. in the manner described in EP-A-0200596.

The values of $K(M'2i)$ and $a(M'2i)$ can be tabulated in the useful intervals of $M'2i$. To carry out such a prior tabulation, a determination takes place of the curves like those of FIG. 1, which involves the fixing of parameters M1 and M2, the calculation of PF (formula (2)) and then I (formula (6)) for different values of the pair (M1, M2).

On the basis of the thus obtained curves and for various values of the parameter M2, determination takes place of K and a. One curve from the group of curves obtained corresponds to a fixed value of M2. A choice is made of two points P1 and P2 of the said curve, which gives two pairs (I(P1), M1(P1) and (I(P2), M1(P2)) respectively associated with these two points. Then, on the basis of formula (7), a system of two equations with two unknowns is obtained and whereof the solution gives K(M2) and a(M2) for the fixed value of M2.

We claim:

1. A system for detecting a substance liable to be contained in an object, comprising:
   a source of irradiation to irradiate said object with neutrons;
   at least one gamma radiation detector to detect gamma radiation emitted by said object;
   an electronic processor to process signals supplied by said gamma radiation detector, said electronic processor being provided for:
   counting the gamma photons corresponding to each line i of a plurality of characteristic lines of at least one chemical element of said substance;
   determining, for each line i, a false detection probability PFi for the chemical element associated with said line, wherein the probability PFi is the probability that the detected signal, corresponding to the said line i, is due to a background noise;
   determining the product of these false detection probabilities;
   comparing said product with a threshold fixed by the system user; and
   notifying said user that the product is below the threshold fixed by said user, the object then being assumed to contain the substance.

2. The system according to claim 1, wherein each probability PFi is determined by the formula:

$$PFi = e^{-M'2i} \sum_{j=Ni+1}^{+\infty} \frac{M'2i^j}{j!}$$

in which Ni represents the count during a time Dt, which corresponds to the line i and which is due to the nuclear reactions induced by the neutrons and also to a background noise M'2i relative to the line i and for the time Dt.

3. The system according to claim 2, wherein each background noise M'2i is determined by forming the sum of a physical background noise M2i, relative to the line i, and the upper limit Ci of counts relative to the said line i, during the time Dt, on objects liable to contain the substance, but known not to contain the substance.

4. The system according to claim 1, wherein said electronic processor is provided for:
determining, for each line i, an information quantity Ii relative to line i and defined by the formula:

$$Ii = -\log \frac{PFi}{1 - PFi}$$

determining the sum of these information quantities;
comparing said sum with a threshold fixed by the system user; and
notifying said user if said sum exceeds the threshold with which it is compared, the object then being assumed to contain the substance.

5. The system according to claim 1, wherein the electronic processor is provided for:
determining, for each line i, an information quantity Ii relative to said line i and defined by the formula:

$$Ii = K(M'2i) \frac{N1i^{a(M'2i)}}{M'2i^{\frac{1}{2}}}$$

in which K and a are stored functions of a background noise M'2i relative to the line i and N1i is the integral part of the difference Ni-M'2i, Ni representing the count, during a time Dt, which corresponds to the line i and which is due to nuclear reactions induced by neutrons and also to the background noise M'2i relative to the line i and for the time Dt;
determining the sum of these information quantities;
comparing said sum with a threshold fixed by the system user; and
notifying said user if said sum exceeds the threshold with which it is compared, the object then being assumed to contain the substance.

6. The system according to claim 1, wherein the irradiation source comprises a fast neutron source and an enclosure for thermalizing these fast neutrons, in which is located the source and which serves to receive the object.

7. The system according to claim 1, wherein the irradiation incorporates a fast neutron source for irradiating the object.

8. The system according to claim 1, wherein said detector comprises a plurality of gamma radiation detectors and that the electronic processor comprises a plurality of detection chains respectively associated with the detectors.

9. The system according to claim 1, wherein said gamma radiation detector is a high resolution detection means.

10. The system according to claim 1, wherein the gamma radiation detector is protected from direct radiation from the irradiation source and wherein said irradiation source is a source of neutrons and said neutrons are collimated towards said object.

11. The system according to claim 1, wherein irradiation source comprises a pulsed neutron source for supplying neutron bursts and wherein said electronic processor cooperates with the detector in order to carry out measurements in time intervals during which it is certain that detection will only take place of one of the categories of gamma photons produced during the irradiation of the object by neutrons.

12. The system according to claim 1, wherein the irradiation source comprises a source of 14 MeV neutrons produced by fusion reactions.

13. A process for detecting a substance liable to be contained in an object, comprising:
irradiating the object with an irradiation source;
detecting gamma radiation emitted by said object with a detector;
processing the signal supplied by said detector, said processing including:
counting the gamma photons corresponding to each line i of a plurality of characteristic lines of at least one chemical element of the substance;
determining, for each line i, a false detection probability PFi for the chemical element associated with said line, wherein the probability PFi is the probability that the detected signal, corresponding to the said line i, is due to a background noise;
determining the product of these false detection probabilities;
comparing said product with a threshold fixed by the system user; and
notifying said user of the product is below the threshold fixed by them, the object then being assumed to contain the substance.

14. The process according to claim 13, wherein each probability PFi is determined by the formula:

$$PFi = e^{-M'2i} \sum_{j=Ni+1}^{+\infty} \frac{M'2i^j}{j!}$$

in which Ni represents the count during a time Dt, which corresponds to the line i and which is due to the nuclear reactions induced by the neutrons and also to a background noise M'2i relative to the line i and for the time Dt.

15. The process according to claim 14, wherein each background noise M'2i is determined by forming the sum of a physical background noise M2i, relative to the line i, and the upper limit Ci of counts relative to the said line i, during the time Dt, on objects liable to contain the substance, but known not to contain the substance.

16. The process according to claim 13, wherein the processing includes:
determining, for each line i, an information quantity Ii relative to line i and defined by the formula:

$$Ii = -\log \frac{PFi}{1 - PFi}$$

determining the sum of these information quantities;
comparing said sum with a threshold fixed by the system user; and
notifying said user if said sum exceeds the threshold with which it is compared, the object then being assumed to contain the substance.

17. The process according to claim 13, wherein the processing includes:
determining, for each line i, an information quantity Ii relative to said line i and defined by the formula:

$$Ii = K(M'2i) \frac{N1i^{a(M'2i)}}{M'2i^2}$$

in which K and a are stored functions of a background noise M'2i relative to the line i and N1i is the integral part of the difference Ni-M'2i, Ni representing the count during a time Dt, which corresponds to the line i and which is due to nuclear reactions induced by neutrons and also to the background noise M'2i relative to the line i and for the time Dt;

determining the sum of these information quantities;

comparing said sum with a threshold fixed by the system user; and notifying said user if said sum exceeds the threshold with which it is compared, the object then being assumed to contain the substance.

18. The process according to claim 13, wherein the object is irradiated by a source including a fast neutron source, and further including an enclosure for thermalizing these fast neutrons, and which serves to receive the object.

19. The process according to claim 13, wherein the irradiation source incorporates a fast neutron source for irradiating the object.

20. A process according to claim 13, wherein the detector comprises a plurality of gamma radiation detectors and that the processing comprises a plurality of detection chains respectively associated with the detectors, and wherein the irradiation source comprises a pulsed neutron source for supplying neutron bursts and in that the electronic processor cooperates with the detector in order to carry out measurements in time intervals during which it is certain that detection will only take place for one of the categories of gamma photons produced during the irradiation of the object by neutrons.

* * * * *